United States Patent [19]

Wiecko

[11] 4,057,548
[45] Nov. 8, 1977

[54] PROCESS FOR PREPARING METHOTREXATE OR AN N-SUBSTITUTED DERIVATIVE THEREOF AND/OR A DI (LOWER) ALKYL ESTER THEREOF AND PRECURSOR THEREFOR

[76] Inventor: Jacek Wiecko, 7031 Ethel St., St. Louis, Mo. 63117

[21] Appl. No.: 671,960

[22] Filed: Mar. 30, 1976

Related U.S. Application Data

[63] Continuation-in-part of Ser. No. 631,134, Nov. 11, 1975, abandoned.

[51] Int. Cl.$^2$ .................................. C07D 471/04
[52] U.S. Cl. ...................... 260/250 BC; 260/250 BN; 424/250; 260/518 R
[58] Field of Search .................. 260/250 BN, 256.4 F, 260/251.5, 250 BC

[56] References Cited

U.S. PATENT DOCUMENTS 2,949,466  8/1960  Hoeffle et al. ............. 260/256.4 F
3,134,778  5/1964  Weinstock et al. ......... 260/256.4 F Primary Examiner—Donald G. Daus
Assistant Examiner—Jose Tovar
Attorney, Agent, or Firm—Roylance, Abrams, Berdo & Kaul

[57] ABSTRACT

There is disclosed a process for the preparation of the pyrazine precursor of methotrexate or an N-substituted derivative thereof and/or a di(lower)alkyl ester thereof having the formula:

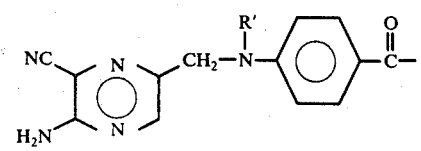

-continued

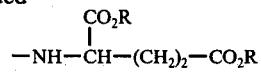

wherein R and R' may each be hydrogen or a lower alkyl group, e.g., ethyl. In a preferred embodiment, the process comprises reacting in one step the compounds aminomalononitrile, β-halopyzuvaldoxime and a di(-lower)alkyl p-methylaminobenzoyl-L-glutamate to form the di(lower)alkyl ester of the pyrazine oxide precursor of methotrexate having the formula:

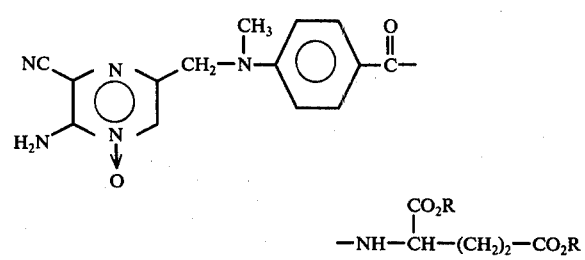

This compound is then treated with either titanium trichloride or iodoformamidinium iodide to deoxygenate the compound. There is also disclosed a process for the preparation of a di(lower)alkyl ester of methotrexate having the formula:

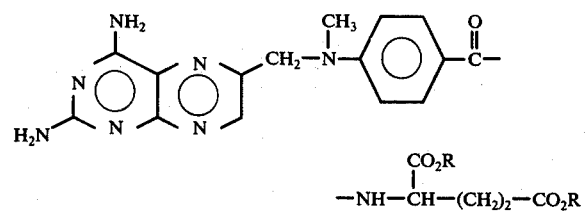

by treating the di(lower)alkyl ester of the pyrazine precursor of methotrexate with a guanidine salt of a weak organic acid, e.g., guanidine acetate.

6 Claims, No Drawings

PROCESS FOR PREPARING METHOTREXATE OR AN N-SUBSTITUTED DERIVATIVE THEREOF AND/OR A DI (LOWER) ALKYL ESTER THEREOF AND PRECURSOR THEREFOR

This application is a continuation-in-part of application Ser. No. 631,134, filed Nov. 11, 1975, now abandoned.

This invention relates to a process for the production of the antineoplastic agent, methotrexate and related compounds.

Methotrexate is a known potent folic acid antagonist useful in the suppression and treatment of acute leukemia and related conditions. This compound has as its principal mechanism of action a competitive inhibition of the enzyme folic acid reductase. Folic acid must be reduced to tetrahydrofolic acid by this enzyme in the process of DNA synthesis and cellular replication. Methotrexate inhibits the reduction of folic acid and interferes with tissue-cell reproduction. Actively proliferating tissues, such as malignant cells, bone marrow, etc. are in general more sensitive to this effect of methotrexate. Cellular proliferation in malignant tissues is greater than most normal tissue and thus methotrexate may impair malignant growth without irreversible damage to normal tissues.

It is difficult to synthesize methotrexate to obtain good yields and to achieve a product of satisfactory purity. One process which has been proposed is shown in the following reaction sequence:

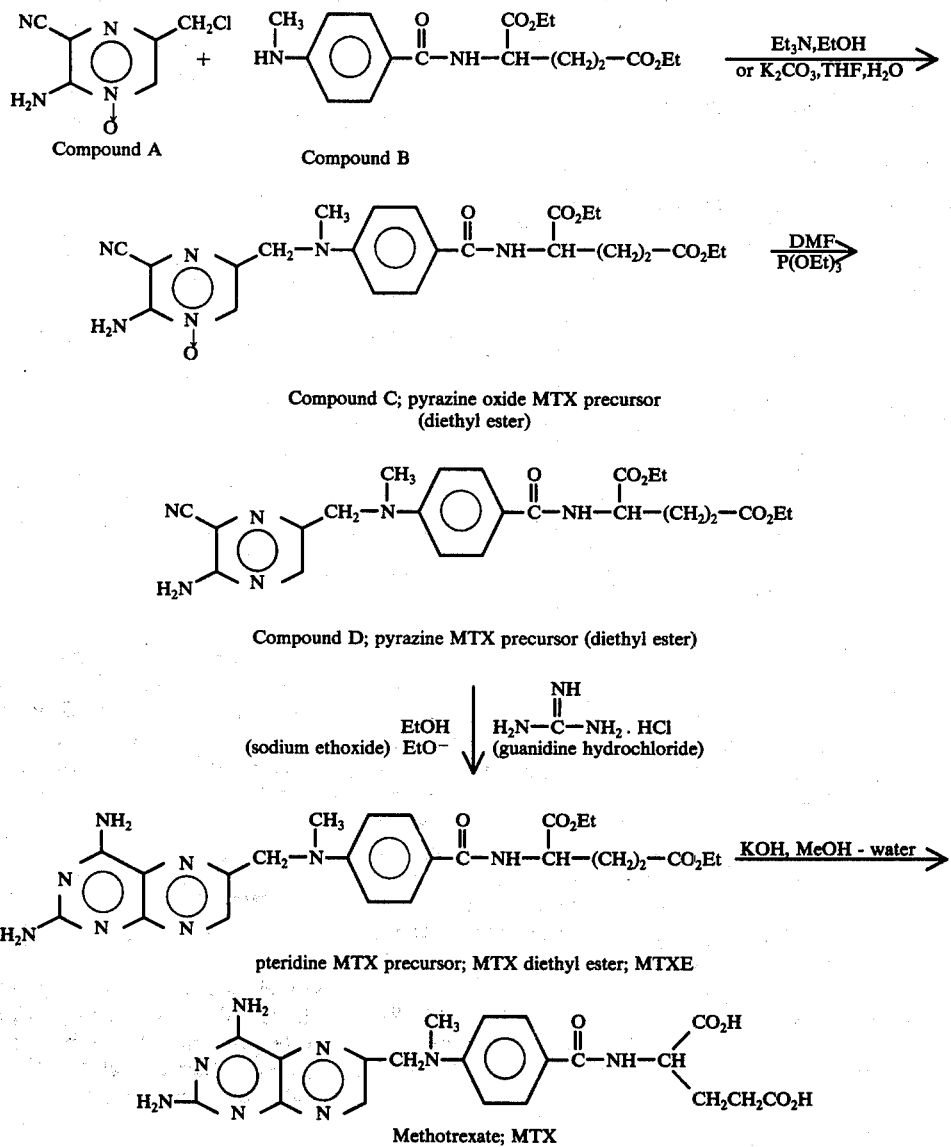

This reaction scheme is unsatisfactory for several reasons. Thus, the conversion of Compound C to Compound D using triethyl phosphite results in a very impure yield of Compound D. Moreover, the conversion of Compound D to the diethyl ester of methotrexate (MTXE) using guanidine hydrochloride in the presence of ethoxide ions is unsatisfactory since the ethoxide ions react to some extent with both Compound D and MTXE in undesirable side reactions to give very impure MTXE. It is then very difficult to isolate MTXE as a pure crystalline solid. Having crystalline MTXE is essential to generate pure methotrexate.

Another process which has been proposed for the preparation of methotrexate is shown in the following reaction sequence:

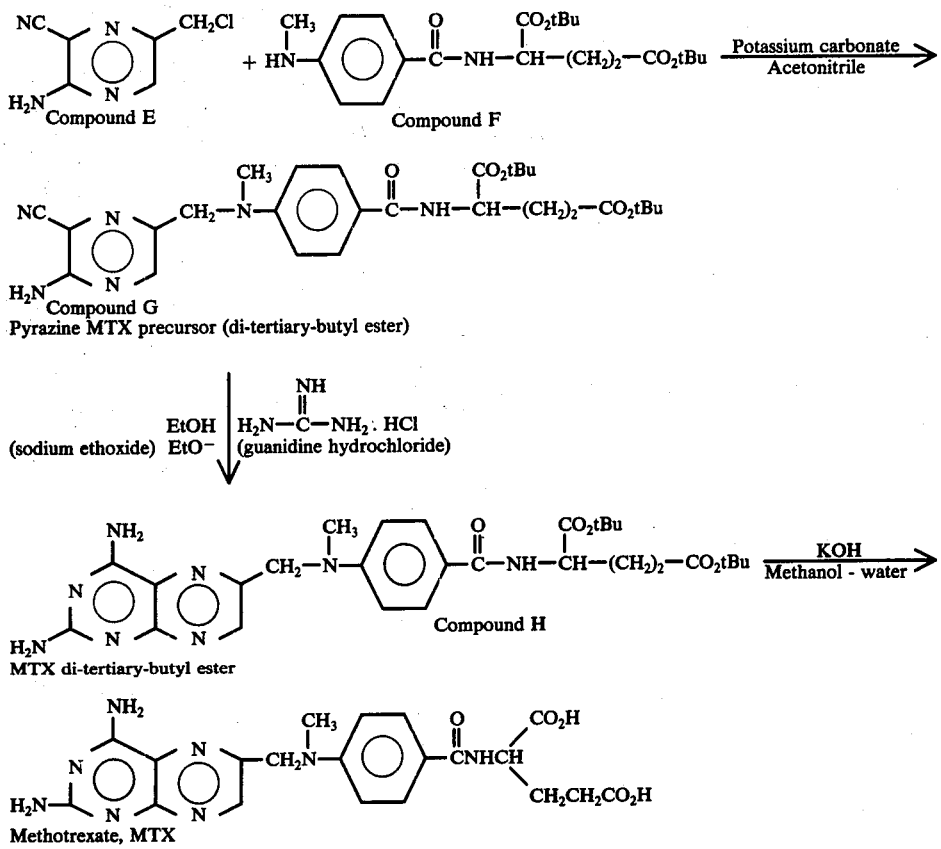

Compound G
Pyrazine MTX precursor (di-tertiary-butyl ester)

MTX di-tertiary-butyl ester

Methotrexate, MTX

By this procedure, it is possible to prepare small quantities of MTXE since both Compound G and Compound H are much easier to isolate as crystalline solids, and thus easier to purify, than is the case with Compound D and MTXE shown in the preceding reaction sequence. However, this sequence is not satisfactory to prepare methotrexate in commercial quantities since Compound E is itself difficult to prepare in pure form in large quantities and Compound F is very expensive to prepare due to the presence of the tertiary butyl function in the compound. Moreover, the presence of ethoxide ions in converting Compound G to Compound H is undesirable for reasons previously mentioned.

It is an object of this invention to provide a new and improved process for the preparation of methotrexate or N-substituted derivative thereof or N-desmethyl derivative thereof of high purity and in good yields.

It is another object of this invention to provide a new and improved process for the preparation of the di(lower)alkyl ester of the pyrazine precursor of methotrexate (Compound D in the first reaction sequence shown above).

It is another object of this invention to provide a new and improved process for the conversion of the di(lower)alkyl ester of the pyrazine precursor of methotrexate to the di(lowe)alkyl ester of methotrexate.

In accordance with the practice of this invention, there are first reacted in one step the compounds (1) aminomalononitrile, (2) β-bromopyruvaldoxime or β-chloropyruvaldoxime and (3) a p-aminobenzoyl-L-glutamic acid or di(lower)alkyl ester thereof having the formula:

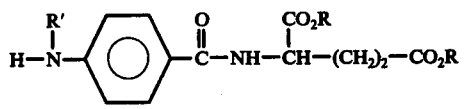

wherein R is a lower alkyl group or hydrogen and R' is a lower alkyl group or hydrogen to form the pyrazine oxide precursor of methotrexate or an N-substituted derivative thereof and/or a di(lower) alkyl ester thereof having the formula:

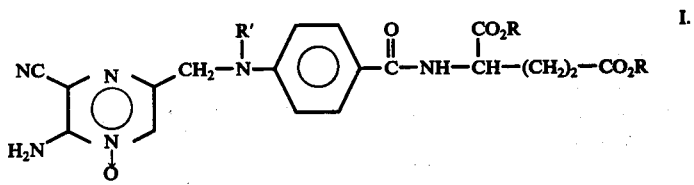

I.

wherein R and R' may each by hydrogen or a lower alkyl group, e.g., methyl, ethyl, propyl, butyl, etc. Aminomalononitrile is preferably used as a salt, e.g., tosylate. By lower alkyl group is meant a group containing up to six carbon atoms. The reaction is preferably conducted in a mixture of water and ethanol and in the presence of sodium bicarbonate. Compound I is then converted to the pyrazine precursor of methotrexate or an N-substituted derivative thereof and/or a di(lower) alkyl ester thereof having the formula:

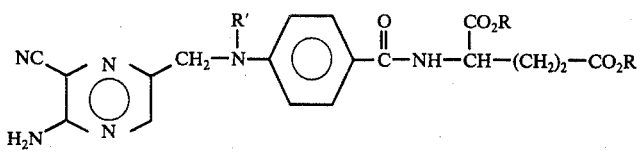

wherein R and R' are the same as previously defined by treating Compound I with either titanium trichloride or iodoformamidinium iodide. In a preferred embodiment, R is ethyl and R' is methyl and Compound I is the diethyl ester of the pyrazine oxide precursor of methotrexate.

Treatment of Compound I with titanium trichloride is preferably conducted in an aqueous-organic medium, e.g., a mixture of water and tetrahydrofuran and in the presence of a buffer such as ammonium acetate. The reaction is also preferably conducted under an inert atmosphere such as nitrogen. After the reaction is complete, it is preferred to add sodium sulfite to convert any excess titanium trichloride to titanium dioxide which can then be removed by filtration.

Treatment of Compound I with iodoformamidinium iodide is preferably conducted by dissolving Compound II in a solvent such as dimethylformamide and slowly adding the iodoformamidinium iodide.

In accordance with another aspect of this invention, Compound II is converted to methotrexate or an N-substituted derivative thereof and/or a di(lower)alkyl ester thereof having the formula:

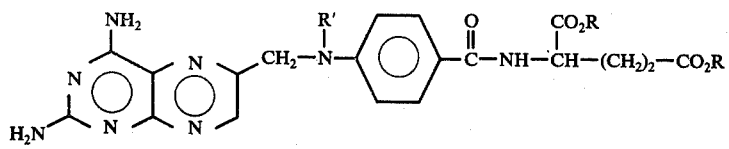

wherein R and R' are the same as previously defined by treating Compound II with a guanidine salt of a weak organic acid, e.g., carbonic acid, oxalic acid, acetic acid or formic acid. Preferably, the reaction is conducted in an inert organic solvent such as dimethylformamide and under an inert atmosphere such as nitrogen.

When Compound III is a di(lower)alkyl ester, it may easily be hydrolyzed, such as in a water-methanol mixture in the presence of potassium hydroxide, to form methotrexate or an N-substituted derivative thereof.

The practice of this invention results in higher yields of both Compound II and Compound III and products of higher purity than prior art processes. Accordingly, much higher yields of methotrexate of high purity can be obtained.

The following examples illustrate the practice of this invention. Example 1 shows the preparation of a product corresponding to Compound II wherein each R is ethyl and R' is methyl.

EXAMPLE 1

Diethyl N-[P[[(2-amino-3-cyano-5-pyrazinyl)methyl]-methylamino]benzoyl]glutamate.

Five g. (15 mmole) of diethyl p-methylaminobenzoyl-L-glutamate and 8.0 g of aminomalononitrile tosylate (65% by nmr assay, 20 mmole) were dissolved in warm ethanol (65 ml., with 15% water by volume). To this solution, cooled to 0° C., was added all at once, and with vigorous stirring, 3.6 g. of β-bromopyruvaldoxime (89% by nmr assay, 19 mmole). After 30 minutes the stirred mixture, which was allowed to warm slowly to room temperature, was neutralized with powdered NaHCO$_3$ to pH 6, stirring continued for four additional hours, and the resulting mixture filtered through Celite. The filtrate was evaporated under reduced pressure to a glass-like substance, which was taken up in 500 ml. of chloroform. The resulting suspension was then filtered using Celite, and the filtrate was washed with water, dried with anhydrous MgSO$_4$, and evaporated to give an orange glass-like substance which was used directly in the next step.

To a 20% solution of titanium trichloride in water (39 mmole), stirred under nitrogen, was added a solution of 18 g. (230 mmole) of ammonium acetate in 55 ml. of water. Then, to this mixture, cooled to 10° C. and stirred with an air-driven stirrer, was added over a period of 5 minutes a solution of the orange glassy substance above dissolved in 60 ml. of tetrahydrofuran. The mixture was vigorously stirred for 15 minutes while a rapid stream of nitrogen was passed through. After this time, 15 g. of powdered sodium sulfite (120 mmole) was added to the mixture, which after several minutes turned from green to yellowish white. This mixture was stirred into 1 liter of chloroform, and the heavy yellow layer separated by use of a separatory funnel. This chloroform layer was washed with water, dried using anhydrous MgSO$_4$, and evaporated under reduced pressure to give a light orange glass, which was then chromatographed rapidly on a column made from 80 g. of Baker silica gel, using 5% ethyl acetate in chloroform as the eluent. The product obtained by evaporation of the eluate was recrystallized from ethanol-ether (1:10) to give a light yellow powder, mp. 85°–88° C. The yield was 4.4 g. (63%).

The following example illustrates the use of iodoformamidinium iodide to deoxgenate the product obtained in the first paragraph of Example 1 instead of titanium trichloride.

EXAMPLE 2

Iodoformamidinium iodide was prepared by chilling 41 ml. of 47% hydriodic acid (0.15 mole) in a 125 ml. Erlenmeyer flask. A solution of 6.35 g. of cyanamide (0.15 mole) in 6.4 ml. of water was added in a rapid stream. There was immediate formation of a straw-colored precipitate. The solution was stirred for two hours while allowing it to warm slowly to room temperature. The product, iodoformamidinium iodide, was collected by filtration, washed with water and dried under high vacuum at room temperature. There was thus obtained 15.75 g. of white crystals representing a 35% yield.

The orange glass-like substance obtained by the procedure described in the first paragraph of Example 1, which is Compound I wherein each R is ethyl and R' is methyl, was dissolved in 20 ml. of dimethylformamide and the stirred mixture was cooled to −20° C. in a nitrogen atmosphere. There was then added 9 g. (30 mmole) of iodoformamidinium iodide and the stirred mixture was allowed to warm to room temperature. After two hours of stirring under nitrogen, the mixture was cooled to −20° C. and 4.4 g. (15 mmole) of additional iodoformamidinium iodide and 4.2 g. (15 mmole) of aqueous hydrogen iodide (45% concentration) were added in portions. The mixture was again allowed to warm to room temperature and stirred for two more hours. After cooling to 0° C., 5 ml. of water and then 12 g. (90 mmole) of sodium sulfite were added and the stirring was continued until the complete disappearance of the brown color, caused by the presence of iodine, took place. The reaction mixture was stirred into 500 ml. of chloroform and washed with aqueous sodium bicarbonate solution. The product was then isolated by chromatography and recrystallization as described in the second paragraph of Example 1.

The following example illustrates the preparation of a compound corresponding to Compound III wherein each R is ethyl and R' is methyl.

EXAMPLE 3

Diethyl N-[p[[(2,4-diamino-6-pteridinyl)methyl]methylamino]benzoyl]glutamate (Amethopterin Diethyl Ester; Methotrexate Diethyl Ester).

A solution containing 4.8 g. (10.2 mmole) of diethyl N-[p[[(2-amino-3-cyano-5-pyrazinyl)methyl]methylamino]benzoyl] glutamate and 5 g. (42 mmole) of guanidine acetate in 40 ml. of dimethylformamide was stirred under notrogen at 120° C. for six hours. The resulting solution was cooled to room temperature, filtered and evaporated to a glassy product using a rotary evaporator and a mechanical vacuum pump to insure a better vacuum. The residual glass was taken up in 500 ml. of chloroform, the resulting suspension filtered using Celite, and the filtrate washed with water, dried using anhydrous MgSO₄, and evaporated to dryness. (The residual material was chromatographed rapidly on a column prepared from 250 g of Baker silica gel using, initially, 2% ethanol in chloroform, and then 5% ethanol in chloroform as eluents.) The material obtained by evaporation of the eluates was crystallized from ethanol-chloroform (4:1) to give small, pale yellow lustrous platelets, mp. 142°-154° C.; yield, 3.8 g. (73%). Further crystallization of this material from ethanol-chloroform (4:1) raised the mp. to 153°-155° C. The compound is completely racemic.

A sample of this product was hydrolyzed in a mixture of water and methanol in the presence of potassium hydroxide. Essentially pure methotrexate was thus obtained.

I claim:

1. A process for preparing a compound having the formula:

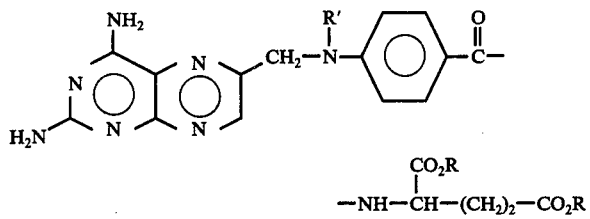

wherein R is hydrogen or a lower alkyl group and R' is hydrogen or a methyl group which consists essentially of the steps of (a) reacting in one step the compounds (1) aminomalononitrile, (2) β-bromopyruvaldoxime or β-chloropyruvaldoxime and (3) a p-aminobenzoyl-L-glutamic acid or di(lower) alkyl ester thereof having the formula:

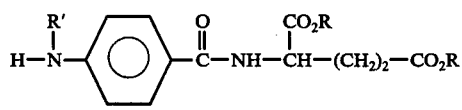

wherein R is a lower alkyl group or hydrogen and R' is a methyl group or hydrogen to form the pyrazine oxide precursor having the formula:

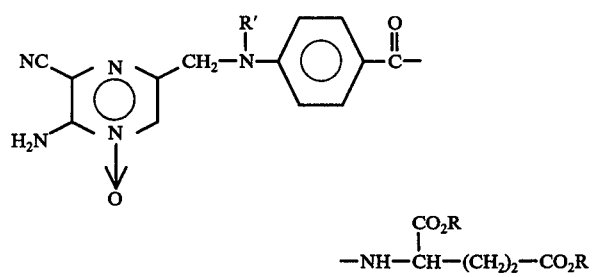

wherein R is a lower alkyl group or hydrogen and R' is a methyl group or hydrogen; (b) treating said compound with either titanium trichloride or iodoformamidinium iodide to deoxygenate said compound; and (c) treating said deoxygenated compound with a guanidine salt of a weak organic acid.

2. A process as defined in claim 1 wherein said salt is guanidine acetate.

3. A process for the preparation of a compound having the formula:

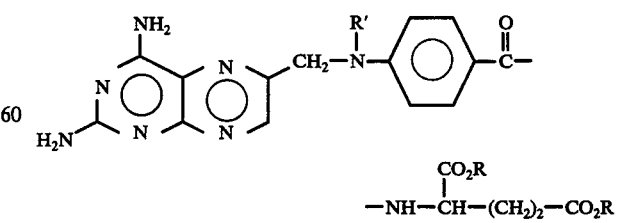

wherein R is hydrogen or a lower alkyl group and R' is hydrogen or methyl which consists essentially of treating a compound having the formula:

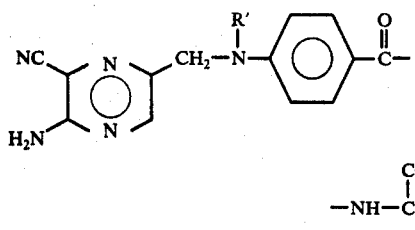

$$-NH-\underset{\underset{CO_2R}{|}}{CH}-(CH_2)_2-CO_2R$$

wherein R is hydrogen or a lower alkyl group and R' is hydrogen or methyl with a guanidine salt of a weak organic acid.

4. A process as defined in claim 3 wherein each R is an ethyl group.

5. A process as claimed in claim 4 wherein said salt is guanidine acetate.

6. A process as defined in claim 5 wherein said reaction is conducted in an inert organic solvent and under an inert atmosphere.

* * * * *